United States Patent
Taggart, II et al.

(10) Patent No.: US 6,965,056 B1
(45) Date of Patent: Nov. 15, 2005

(54) REMOVAL OF SALTS IN THE MANUFACTURE OF PHENOLIC COMPOUND

(75) Inventors: Austin Dale Taggart, II, Houston, TX (US); Edgar Donald Allan, Katy, TX (US); Roberto Carlos Longoria, Houston, TX (US); David Werner Daum, Seabrook, TX (US); Robert Lawrence Blackbourn, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/304,298

(22) Filed: May 3, 1999

(51) Int. Cl.$^7$ .............................................. C07C 37/68
(52) U.S. Cl. ..................................... 568/754; 568/768
(58) Field of Search ................................ 568/754, 768

(56) References Cited

U.S. PATENT DOCUMENTS

| | | | |
|---|---|---|---|
| 2,715,145 A | * | 8/1955 | Bewley |
| 2,727,074 A | * | 12/1955 | Bewley |
| 2,951,870 A | * | 9/1960 | Cooke .......................... 568/754 |
| 3,467,721 A | | 9/1969 | Bewley ........................ 260/621 |
| 3,850,996 A | * | 11/1974 | Nixon |
| 3,931,339 A | | 1/1976 | Cooke .......................... 260/621 |
| 4,207,264 A | | 6/1980 | Anderson et al. |
| 4,262,150 A | | 4/1981 | Pujada .......................... 568/754 |
| 4,262,151 A | | 4/1981 | Pujado .......................... 568/754 |
| 4,283,568 A | | 8/1981 | Pujado .......................... 568/754 |
| 4,328,377 A | | 5/1982 | Mori et al. .................... 568/798 |
| 4,351,967 A | | 9/1982 | Nishimura et al. |
| 4,434,305 A | * | 2/1984 | Kurosaka |
| 5,283,376 A | * | 2/1994 | Dyckman .................... 568/574 |
| 5,510,543 A | | 4/1996 | Fulmer et al. ............... 568/754 |
| 5,847,235 A | * | 12/1998 | Dyckman .................... 568/754 |
| 5,962,751 A | * | 10/1999 | Dyckman .................... 568/574 |

FOREIGN PATENT DOCUMENTS

| | | |
|---|---|---|
| EP | 0085289 A1 | 8/1983 |
| EP | 0816335 A1 | 1/1998 |
| JP | 5 6099-430 | 8/1981 |

* cited by examiner

*Primary Examiner*—Michael L. Shippen (57) ABSTRACT

There is provided a process for the manufacture of phenolic compounds by separating a neutralized aralkyl hydroperoxide cleavage mass stream containing salts of neutralization into a crude ketone stream and a crude phenolic stream containing the salts of neutralization; separating the crude phenolic stream into a concentrated phenolic-rich stream, enriched in phenolic compounds, and a crude phenolic bottoms stream enriched in tars and alpha methyl styrene dimers, each compared to the crude phenolic stream, said crude phenolic bottoms stream containing salts of neutralization; to the crude phenolic bottoms stream, adding water and a diluent composition, thereby forming a phase separable crude phenolic bottoms stream, said diluent composition comprised of hydrocarbons phase compatible with the crude phenolic bottoms stream and having a combined density lower than the density of the crude phenolic bottoms stream; separating the separable crude phenolic bottoms stream into a hydrocarbon phase and an aqueous phase containing salts of neutralization; whereby the amount of salts of neutralization in the hydrocarbon phase is reduced compared to the amount of salts of neutralization present prior to separation.

128 Claims, 1 Drawing Sheet

FIG.1

REMOVAL OF SALTS IN THE MANUFACTURE OF PHENOLIC COMPOUND

1. FIELD OF THE INVENTION

The present invention relates to a process for separating products contained in an alkyl hydroperoxide cleavage mass, and in particular, to a process for the removal of salts of neutralization present in a cleavage mass for the manufacture of phenol.

2. BACKGROUND OF THE INVENTION

In general, phenol is manufactured by oxidizing an alkyl substituted aromatic compound, such as cumene, to form the hydroperoxide derivative thereof, followed by cleavage of the hydroperoxide with a mineral acid such as sulfuric acid to form a cumene hydroperoxide cleavage mass. The cleavage mass generally contains species such as phenol, acetone, α-methyl styrene (AMS), cumene, cumyl phenol (CP), dimethylbenzyl alcohol (DMBA), acetophenone (AP), AMS dimers (AMSd), tars and heavies, and mineral acid such as sulfuric acid. Prior to separating out the different species and recovering acetone and phenol, the cleavage mass is neutralized with a caustic, such as sodium hydroxide, to prevent the acidic cleavage mass from corroding downstream equipment. Much of the salt is separated and removed from the process in a wash/phase separation step prior to feeding the partially or wholly neutralized cleavage mass to a splitter and further purification columns. However, a significant quantity of salt remains in the cleavage mass entering the splitter, and this quantity of salt becomes more concentrated as the stream passes from one purification column to the next.

In the course of making phenol, the fully or partially neutralized cleavage mass passes through several distillation and purification columns to ultimately form a stream of heavy by-products. The heavy by-product stream may be subject to cracking, and the bottoms of the cracker are usually incinerated. The heavy hydrocarbon by-product stream feeding a cracker or furnace, however, contains a high concentration of the salts of neutralization, typically sodium sulfate. The salts remaining after the wash/phase separation step are carried into the splitter, which separates out ketone as an overhead from phenol as a phenol bottoms stream, into the phenol bottoms stream and into further downstream equipment through the bottoms stream of each purification column, all the way to the cracker or furnace. It is in the cracker and furnace, and in the reboiler for the cracker, where the salts of neutralization settle and are no longer carried through. The settling of the salts in the cracker, reboiler, and furnaces causes operating problems, requiring intermittent shut down to clean the equipment or replace parts. The salts also degrade the value of a tarry mass as fuel for burning. Therefore, it is highly desirable to remove as much salt as possible prior to feeding a cracker or furnace.

Many methods have been proposed for removing salts of neutralization in the manufacture of phenol. One such method, disclosed in U.S. Pat. No. 4,328,377, involves feeding a neutralized cleavage mass to a multi-tray (20 or more) splitter, separating out the ketone as an overhead from a bottom fraction comprised of a crude phenol stream, and recovering the phenol, wherein a liquid layer located near or below the cleavage mass feed site but above the bottoms is withdrawn from the splitter column, phase separating the liquid layer into an oil layer and an aqueous layer containing the salts of neutralization, and recycling the oil layer back to the splitter column at a site below the liquid layer withdrawal site. To enhance the ability of the liquid layer to phase separate, a hydrocarbon having a lower boiling point than phenol and a specific gravity difference of at least 0.03 is added to the liquid layer.

A disadvantage of this process is that large quantities of liquid layer must be removed and processed to sufficiently reduce the amount of salt to the desired level. For example, for every 100 parts by weight per hour of cleavage mass fed to the mutli-tray splitter, 127 parts by weight per hour of a liquid sidedraw was processed in a phase separator. Treating such large amount of liquid requires adding and processing corresponding large quantities of water, and adding large quantities of lower specific gravity hydrocarbon, processing large amounts of oil layer, and increasing the volume of the phase separation vessel. It would be desirable to discharge the salts of neutralization from the process by feeding a phase separator with a small amount of hydrocarbon, discharging low amounts of water containing the salts of neutralization from the process while effectively removing at least 80% of the salts of neutralization from the process, using low amounts of lower density hydrocarbon to enhance phase separation, concentrating the salt in a purge stream discharged from a phase separator to high levels, and/or employing a smaller phase separation vessel. It would also be desirable to employ a process for manufacturing phenol where the amount of water or lower density hydrocarbon lost from the process is minimized or eliminated.

3. SUMMARY OF THE INVENTION

In one embodiment of the invention, there is provided a process for the manufacture of phenolic compounds comprising:

a) separating a neutralized aralkyl (aryl alkyl or alkyl aryl) hydroperoxide cleavage mass stream containing salts of neutralization into a crude ketone stream and a crude phenolic stream containing the salts of neutralization;

b) separating the crude phenolic stream into a concentrated phenolic-rich stream, enriched in phenolic compounds, and a crude phenolic bottoms stream enriched in tars and alpha methyl styrene dimers, each compared to the crude phenolic stream, said crude phenolic bottoms stream containing salts of neutralization;

c) to the crude phenolic bottoms stream, adding water and a diluent composition, thereby forming a phase separable crude phenolic bottoms stream, said diluent composition comprised of a hydrocarbon phase compatible with the crude phenolic bottoms stream and having a combined density lower than the density of the crude phenolic bottoms stream;

d) separating the separable crude phenolic bottoms stream into a hydrocarbon phase and an aqueous phase containing salts of neutralization;

whereby the amount of salts of neutralization in the hydrocarbon phase is reduced compared to the amount of salts of neutralization present prior to separation.

In another embodiment of the invention, there is provided a process for the manufacture of phenolic compounds comprising wholly or partially neutralizing an aralkyl hydroperoxide cleavage mass feed containing an acid and having a pH of less than 6 in neutralization zone, thereby forming an aqueous neutralized aralkyl hydroperoxide cleavage mass containing salts of neutralization, subsequently separating said aqueous neutralized aralkyl hydroperoxide cleavage mass into an aqueous stream and a neutralized aralkyl hydroperoxide cleavage mass stream containing a smaller amount of salts than in the aqueous stream, subsequently separating the aralkyl hydroperoxide cleavage mass into a crude ketone stream and a crude phenolic stream containing the salts, separating said crude acetone stream into a concentrated ketone rich stream and a crude ketone bottoms stream, separating said crude phenolic stream into a concentrated phenolic-rich stream and a crude phenolic bottoms stream, and ultimately separating from the crude phenolic bottoms stream a light ends stream and a tarry stream containing an amount of salts reduced by at least 90% of the amount of salts contained in the crude phenolic bottoms stream, and recycling at least a portion of said crude ketone bottoms stream and at least a portion of said light ends stream as feeds to said aralkyl hydroperoxide cleavage mass, said aqueous neutralized aralkyl hydroperoxide cleavage mass, or to both.

In yet another embodiment of the invention, there is provided a composition comprising at least 40 wt. % water, less than 20 wt. % phenolic compounds, alkali metal salts in an amount of at least 1.5 wt. %, phenolic tars, and α-methyl styrene dimers, wherein the volume ratio of water to all ingredients in said composition other than water is between 1:1 to about 3:1.

In yet a further embodiment of the invention, there is provided a process for removing salts of neutralization present in a neutralized aralkyl hydroperoxide cleavage mass comprising removing 80 wt. % or more of said salts from said cleavage mass through one or more aqueous streams discharged and purged from said process, the combined flow rate of all aqueous purge stream(s) containing the salts being less than 5 parts by weight per hour based on a flow rate of 100 parts by weight per hour of the cleavage mass fed to a means for separating said cleavage mass into a crude ketone stream and a crude phenolic stream.

There is also provided an embodiment for manufacturing phenolic compounds comprising feeding a neutralized aralkyl hydroperoxide cleavage mass containing salts of neutralization to a splitter, separating acetone and phenol from said cleavage mass in the splitter, removing all or a portion of the phenol from the splitter, followed by feeding said all or a portion of said phenol to a phase separation vessel having a volume of 5000 gallons or less, based on 100 parts by weight per hour of cleavage mass feed to the splitter, and removing at least 80 wt. % of the salts of neutralization from said phenol.

In another embodiment, there is provided a process for removing salts of neutralization, comprising feeding an aralkyl hydroperoxide cleavage mass containing salts of neutralization to a splitter, separating acetone from a crude stream of phenol in said splitter, followed by feeding a portion or all of said crude phenol stream to a phase separator as a feed comprising hydrocarbons, water, and salts of neutralization, the total amount of hydrocarbon feed from any source to said separator being less than 10 parts by weight per hour, based on 100 parts by weight per hour of said cleavage mass fed to the splitter, wherein at least 80 wt. % of the salts of neutralization are removed from the crude phenol stream.

In another embodiment of the invention, there is provided a process for removing salts of neutralization from an aralkyl hydroperoxide cleavage mass containing salts of neutralization comprising separating acetone from said cleavage mass, followed by purging the salts of neutralization in an aqueous purge stream comprising at least 3 wt. % of the salts of neutralization and at least 90 wt. % water, based on the weight of the purge stream.

In a further embodiment of the invention, there is provided a process for making phenol comprising feeding an aralkyl hydroperoxide cleavage mass containing salts of neutralization into a splitter and separating the cleavage mass in the splitter into a ketone stream and a phenol stream containing the salts, optionally concentrating the phenol stream by further distillation, and forming a phase separable hydrocarbon stream from said phenol stream comprising adding a net amount of water of 5 parts by weight per hour or less to the phenol stream, based on 100 parts by weight per hour of cleavage mass fed to the splitter, phase separating the phase separable hydrocarbon stream into an aqueous stream and a hydrocarbon stream, and discharging a portion or all of the aqueous stream from the process as an aqueous purge stream, wherein at least 80 wt. % of the salts of neutralization present in the cleavage mass entering the splitter are removed through said purge stream.

The various features of the invention are described in further detail below.

5. DETAILED DESCRIPTION OF THE INVENTION

Figure 1:
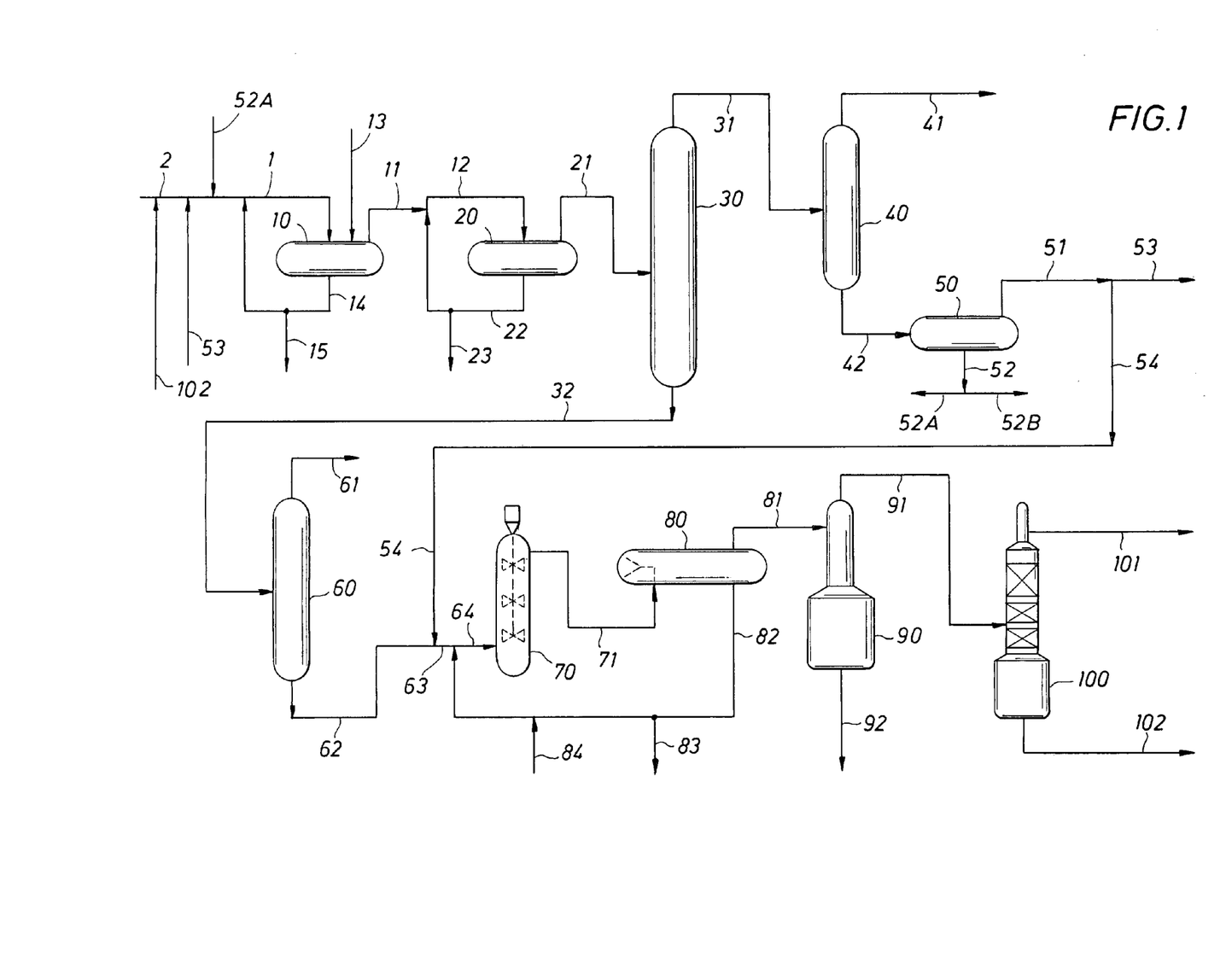
FIG. 1 is a process flow diagram of that portion of the process for the separation of products contained in an alkyl hydroperoxide cleavage mass.

A more detailed understanding of the invention may be had by reference to FIG. 1, which illustrates features of the invention as well as more preferable embodiments of the invention.

FIG. 1 is an illustration of a process directed towards separating the by-products contained in a cumene hydroperoxide cleavage mass into streams of acetone, phenol, α-methyl styrene (AMS), cumene, aqueous streams containing salts of neutralization such as $NaSO_4$, cumyl phenol (CP), dimethylebenzyl alcohol (DMBA), acetophenone (AP), AMS dimers (AMSd), and tars and heavies. Those of ordinary skill in the art will appreciate that other vessels not depicted in FIG. 1 may be included in the process of the invention, such as further distillation columns for additional purification, additional phase separators, coolers, heat exchangers, pumps, and storage vessels where desired. Thus, other purification columns may be introduced prior to or after each successive description where products contained in a particular stream are separated. For example, describing the separation of a light ends stream from a tarry stream in a crude phenol bottoms stream does not restrict the inclusion of any number of prior purification columns introduced to further purify the crude phenol bottoms stream prior to the point at which a tarry stream is extracted.

Turning to FIG. 1, while reference may be had to a cumene hydroperoxide cleavage mass flowing through line (2), the invention also includes processing an aralkyl hydroperoxide cleavage mass. The aralkyl hydroperoxide used in the process of this invention includes compounds represented by formulas 1 and 2 below:

(1)

(2)

wherein Ar represents an aromatic ring, preferably a phenyl ring, and R1, R2, R3 and R4 independently represent a lower linear or branched alkyl group having 1–4 carbon atoms. Specific examples of the aralkyl hydroperoxide are cumene hydroperoxide, p-cymene hydroperoxide, m-cymene hydroperoxide, sec-butylbenzene hydroperoxide, p-ethylisopropylbenzene hydroperoxide, isopropylnaphthalene hydroperoxide, m-diisopropylbenzene dihydroperoxide and p-diisopropylbenzene dihydroperoxide. Cumene hydroperoxide, p-cymene hydroperoxide and m-cymene hydroperoxide are preferred. Cumene hydroperoxide is most preferred.

The cleavage mass is acidic due to the addition of a mineral acid, such as sulfuric acid, to the aralkyl hydroperoxide to effect cleavage of the hydroperoxide into a ketone compound, such as acetone, and a phenolic compound, such as phenol, along with the other byproducts noted above. Examples of the mineral acid used to cleave the hydroperoxide into a phenolic compound and a ketone compound include sulfuric acid, hydrochloric acid, phosphoric acid and mixtures of these. Sulfuric acid is the most common agent used.

The phenolic compound, which is one of the desired acid cleavage products of the process, is represented by the formula Ar—OH or HO—Ar—OH corresponding to formula (1) or (2). Specific examples include phenol, p-cresol, m-cresol, ethylphenol, naphthol, hydroquinone and resorcinol. Phenol, p-cresol and m-cresol are preferred, and phenol is most preferred.

The ketone compound, another desirable acid cleavage byproduct, is expressed by formula 3:

(3)

Examples include acetone and methyl ethyl ketone, preferably acetone.

Any known method can be employed to cleave the hydroperoxide with a mineral acid. Industrially, the cleavage reaction is usually performed in the presence of a hydrocarbon solvent. An aromatic hydrocarbon is preferred as the hydrocarbon solvent, and specific examples include benzene, toluene, xylene, cumene, cymene, ethylbenzene, phenol, diisopropylbenzene, butylbenzene, alpha-methylstyrene and isopropenyltoluene. The temperature of the acid cleavage is not particularly restricted. Advantageously, it is generally about 50° C. to about 100° C., preferably about 70° C. to about 90° C. Generally, the amount of the mineral acid is 0.005 to 2 parts by weight, preferably 0.01 to 0.1 parts by weight, per 100 parts by weight of the hydroperoxide to be cleaved.

The mineral acid contained in the reaction mixture obtained by the acid cleavage of the hydroperoxide is then neutralized or removed. The particular method of neutralization is not limited. The acidic cleavage mass stream is fed to a neutralizer (10), where residual sulfuric acid is neutralized either partially or wholly by addition of a caustic through line (13). By a neutralized cleavage mass is meant a cleavage mass which is partially or wholly neutralized. Neutralization of the acid cleavage mixture of the hydroperoxide can be performed by any desired known method. The caustic may be added to line (2) prior to entry into neutralizer (10) or directly to the neutralizer (10). A typical caustic is an aqueous sodium hydroxide stream and/or sodium phenolate.

The salt formed as a result of the neutralization of the acid cleavage needs not always to be separated and removed from the cleavage mass. However, it is common to remove a portion of the salts prior to feeding the cleavage mass to the splitter (30). Methods include contacting the acid cleavage mixture with an aqueous solution of a strong alkali such as sodium hydroxide or sodium phenolate and then optionally removing the water layer by in a phase separator; or contacting the acid cleavage mixture with an aqueous solution of a strong alkali such as sodium hydroxide, removing the aqueous layer through phase separation, followed by washing the hydrocarbon oily layer with water to remove more salt; or a method where the neutralized cleavage mass is filtered to remove the salt precipitated in solid form.

In a particular embodiment of the invention, reference may be had to the design depicted in FIG. 1. In the neutralizer (10), the sulfuric acid present in the hydrocarbon phase of the cleavage mass forms a Na$_2$SO4 salt in the aqueous phase which leaves the neutralizer through line (14). A portion of the salty aqueous stream may be recirculated back to the neutralizer through line (14), and a portion may be discharged through line (15). The conditions within the neutralizer (10) may vary depending upon the number of neutralizers, wash drums, and phase separators one may employ, but typical conditions are to maintain the pH between 5 and 8 at 1 or more atmospheres and at a temperature ranging from 35° C. to 55° C. Other conditions and equipment, such as those specified in U.S. Pat. Nos. 5,510,543; 3,931,339; 4,262,150; and 4,262,151 are also suitable, and each are herein incorporated by reference in full. For example, if desired, the cleavage mass may be only neutralized up to a pH within the range of 4–5.

The hydrocarbon phase leaves the neutralizer (10) through line (11) and is fed into a wash drum (20) through line (12). In addition to adjusting the pH back to a range of 5–7, the wash drum washes the residual Na$_2$SO$_4$ salts remaining in the hydrocarbon phase with water, a portion of which is discharged and a portion of which may be recirculated back to the wash drum (20) by joining with line (11).

In spite of the many efforts at effecting a substantially complete removal of salts, residual amounts of salts remain within the hydrocarbon stream. The amount of salt left in a composition of neutralized aralkyl hydroperoxide cleavage mass prior to entering the splitter will vary depending upon the degree of neutralization and the efficiency of the separation techniques used to remove the salt in a phase separation and/or wash step. The process of the invention can be used to remove salt at any level. Typical amounts of salt in a neutralized cleavage mass range from 1000 ppm to 10,000 ppm. The amount of salt is generally reduced within a range of 300 ppm to several thousand ppm salt. In the process of the invention, the amount of salt can be reduced to even smaller quantities of salt, in the range of 25 ppm to 300 ppm, preferably from 25 ppm to 120 ppm.

The neutralized and optionally washed cumene hydroperoxide cleavage mass is fed to the splitter (30) through line (21) where the cleavage mass is separated through, for example, distillation, into a crude phenolic stream and a crude acetone stream. The crude acetone stream removed from the splitter at the overhead through line (31) is rich in acetone, meaning that acetone is the predominant species in the stream by weight. Small amounts of water and other higher boiling compounds such as AMS, cumene, some aldehydes, and un-neutralized organic acids may also be present in the crude acetone stream. Some of the lighter boiling impurities, such as other aldehydes, may optionally be removed from the composition by distillation and optionally recycled back along with acetone caught up in the overhead to a cleavage zone where the aralkyl hydroperoxide is cleaved.

Whether or not distilled, the crude acetone stream is fed through line (31) ultimately to an acetone finishing column (40) where the crude acetone stream is separated by distillation into a concentrated acetone stream enriched in acetone over the amount of acetone present in the crude acetone stream and into a crude acetone bottoms stream. The concentrated acetone stream is removed from the finishing column (40) through line (41), while the crude acetone bottoms stream is removed at the bottom of the column (40) through line (42). Optionally, caustic may be added to the finishing column (40) to react the aldehyde to heavier compounds, thereby facilitating removal by distillation.

The crude acetone bottoms stream is comprised of water, organic acids, AMS, and cumene. To separate water from the hydrocarbons in the crude acetone bottoms stream, it is useful to feed the stream to a phase separator (50) wherein water and the salts of the organic acid are separated and discharged as an aqueous phase through line (52) from the hydrocarbon phase, which leaves the separator (50) through line (51). Optionally, a portion of the aqueous phase discharged from separator (50) may be recycled back to line (1) through line (52A) to reduce the amount of fresh water feed that is added to the phase separator/wash drum. The other portion is sent to treatment for dephenolation through line (52B).

The crude acetone bottoms stream in line (51) from which water has optionally been removed is comprised of AMS, cumene, and other hydrocarbon compounds having boiling points lower than phenol. Part of the crude acetone bottoms stream, whether processed through the phase separator (50) or not, is used to feed the neutralizer (10) through line (53) in order to facilitate phase separation between the cleavage mass and water. The amount of crude acetone bottoms stream fed to the neutralizer (10) through line (53) may range anywhere from 5 wt. % to 40 wt. % based on the weight of the cleavage mass stream. The crude acetone bottoms stream may be fed and mixed into line (1) or may be fed directly into the neutralizer. Optionally, the crude acetone bottoms stream be fed to the wash drum (20) as well.

Another portion of the crude acetone bottoms stream from the acetone finishing column (40) or from the phase separator (50) may be fed as a diluent to line (62) described further below in greater detail.

The crude phenol stream exits the bottom of the splitter (30) through line (32). The predominant species in the crude phenol stream is phenol, usually in amounts exceeding 85 wt. % based on all ingredients in the crude phenol stream. The salts of neutralization ($Na_2SO_4$) present in the cumene hydroperoxide cleavage stream in line (21) pass through the splitter (30) into the crude phenol stream. Accordingly, the amount of salts usually ranges from be 80–230 ppmw based on the weight of all ingredients in the crude phenol stream as measured at line (32), or from 0.05 to 0.3 wt. % based on the weight of all ingredients in the crude phenol stream as measured at line (62). Other ingredients present in the crude phenol stream include AP, CP, AMSd, DMBA, and tars and heavies.

A substantial amount of the phenol present in the crude phenol stream is removed by feeding the stream in line (32) into a crude phenol column (60) where phenol is separated by distillation into a concentrated phenol rich stream which is enriched in the weight percentage of phenol compared to the weight percentage of phenol present in the crude phenol stream, and into a crude phenolic bottoms stream enriched in tars and AMSd compared to the weight percent of tars and AMSd present in the crude phenol stream. The concentrated phenol rich stream exits the column (60) through line (61) for finishing, while the crude phenol bottoms stream exits the bottoms of the column (60) through line (62).

The typical composition of the crude phenol bottoms stream is as follows:

| | |
|---|---|
| Phenol: | 15–35 wt. % |
| AP: | 10–25 wt. % |
| DMBA: | 2–8 wt. % |
| CP: | 15–25 wt. % |
| AMSd: | 4–15 wt. % |
| Tars/Heav: | 12–25 wt. % |
| Salts: | 0.05–0.3 wt. % |

To the crude phenol bottoms stream is added water and a diluent composition which is phase compatible with the crude phenolic bottoms stream in order to form a phase separable crude phenolic bottoms stream. For measurement purposes only, a stream becomes phase separable when a standing batch, without agitation, phase separates into a hydrocarbon phase and an aqueous phase containing at least 80 wt. % of salts of neutralization without agitation within a period of 0.5 hours or less. A phase separable crude phenolic bottoms stream is one in which a hydrocarbon phase and an aqueous phase containing at least about 80 wt. % of the salts of neutralization, as measured by allowing the stream to stand without agitation, can be separated in less than one hour residence time.

The hydrocarbon portion of the diluent stream consisting of all hydrocarbons in the diluent stream have a combined lower density than the density of the crude phenolic bottoms stream under the conditions existing in the bottoms phase separator (80). While the diluent stream can be derived from any source, it is advantageous to recycle a portion of the crude acetone bottoms stream comprised of cumene and AMS through line (54) into the crude phenol bottoms stream in line (62). The hydrocarbons in the diluent stream in line (54) comprised of cumene and AMS flow through the process ultimately into line (102) from the distillation in the rectifier (100), and fed to the neutralizer (10), thereby closing the loop on the flow of the hydrocarbon portion of the diluent stream through the process with minimal discharge.

As an example, the density of the crude phenol bottoms stream may be on the order of 54–58 pcf at temperatures ranging from 180–210° C. and at pressures sufficient to keep the stream in liquid state. Although phenol has a higher density than water, it is also readily miscible with water, rendering it difficult to obtain satisfactory phase separation between the hydrocarbon phase and the aqueous phase in a phase separation operation designed to remove the salts of neutralization. Accordingly, a hydrocarbon diluent having a lower density that the density of the crude phenol bottoms stream is added to enhance phase separation between the hydrocarbon and aqueous phase. This method of enhancing phase separation is more effective at removing salts than a method of increasing the salt concentration because by increasing the salt concentration, the amount of salt distributed into the hydrocarbon phase is increased and the effectiveness of the unit operation is reduced.

Diluents which are phase compatible and readily miscible with phenol, have a lower density than phenol, and which are phase incompatible with water under the operating conditions of the phase separator are preferred. Such diluents will attract solubilized phenol from the aqueous phase into the hydrocarbon phase. A diluent composition having a combined hydrocarbon density of 51–53.5 pcf comprised of 60–90 wt. % cumene, 10–30 wt. % of AMS, and optionally less than 10 wt. % of other hydrocarbons and no water is but one example, but is a preferred composition because it is readily obtainable as an extract from the acetone finishing operation. Optionally, if desired, the diluent composition may be recycled directly from the acetone finishing column (40) to line (62) without first removing water. Another example of a suitable diluents include a stream of cumene or a stream of AMS, each as a fresh feed or derived from any source in the process.

While a diluent hydrocarbon stream having a lower density than the crude phenol bottoms stream must be added to obtain satisfactory phase separation, the density difference need not be large. Although the invention is not restricted to a particular density difference, an advantage of the invention is that the hydrocarbon phase may be effectively separated from the aqueous phase in the phase separator (80) when the density difference between the two is only 1–2 pcf. This advantage is achieved due to the low percentage of phenol present in the crude phenolic bottoms stream. A stream comprised of 85 wt. % or more phenol would require the use of a diluent having a larger density delta to effectively phase separate the aqueous phase due to the ready miscibility between phenol and water.

An additional advantage to the invention is that the volume amount of diluent needed to provide a phase separable stream is low compared to the volume of diluent that would be needed if one attempted to create a phase separable stream from a stream exiting the splitter (30) as either a side-draw or from a bottoms, as in line (32). Since a large volume of compounds in the cleavage stream in line (21) are removed in the splitter (30) through line (31), and the volume of the crude phenol stream in line (32) is reduced further by removal of phenol through the crude phenol column (60) into line (61), the process provides the advantage of needing only low amounts of diluent to effect satisfactory phase separation.

Specifically, for every 100 part by weight per hour of cleavage mass fed through line (21) into the splitter (30), less than 3 parts by weight per hour of diluent is advantageously needed to make a phase separable crude phenol bottoms stream, preferably less than 2, and even as little as 1.5 parts by weight per hour or less, each based on 100 parts by weight per hour of aralkyl hydroperoxide cleavage mass stream and discounting any water present in the phase separable crude phenol bottoms.

The amount of diluent added relative to the amount of crude phenol bottoms stream is sufficient to phase separate the hydrocarbon phase from the aqueous phase. While there is no upper limit, the more diluent added, the higher the loading of material through downstream equipment which must be processed and handled. Suitable weight ratios of diluent composition to crude phenol bottoms composition are at least 0.15:1, more preferably 0.3:1, most preferably from 0.45–0.6:1. The specific amount of diluent is balanced between keeping the loading factor low while providing sufficient diluent to efficiently phase separate.

A diluted crude phenolic bottoms stream composition may comprise:

| | |
|---|---|
| AMS: | 3–10 wt. % |
| Cumene: | 10–40 wt. % |
| Phenol: | 5–25 wt. % |
| AP: | 7–20 wt. % |
| DMBA: | 1–5 wt. % |
| CP: | 7–20 wt. % |
| AMSd: | 3–10 wt. % |
| Tars/Heav: | 6–20 wt. % |
| Salts: | 0.05–0.25 wt. % |

Since relatively small amounts of feed to the phase separator are effective to remove 80 wt. % or more of salts of neutralization, the overall volumetric hydrocarbon flow to the phase separator (80) is also very low. By hydrocarbon is meant any compound in a stream other that water. In particular, the flow rate of all hydrocarbons to the phase separator from any source need only be on the order of less than 10, preferably less that 7, more preferably 6, most preferably 5 or less parts by weight per hour based on 100 parts by weight per hour of total cleavage mass feed to the splitter (30), to effectively separate and discharge at least 80 wt. %, more preferably at least 90 wt. % of the salts of neutralization from the phase separator into a salty aqueous purge stream.

In addition to a diluent stream, water is added to the crude phenol bottoms stream as the additional ingredient to further enhance the ability of the crude phenol bottoms stream to phase separate. As depicted in FIG. 1, water is added to the diluted crude phenol bottoms stream in line (63) through line (82) after the diluent has been added, to make the phase separable crude phenol bottoms stream. The amount of water should be kept as low as possible to concentrate the salts and avoid loading the system with excess water and avoid loss of phenol to the aqueous phase since phenol and water are miscible, while on the other hand, facilitating removal of salts from the hydrocarbon phase by increasing the difference in density between the phases. It is within the ordinary skill to acquire an optimal range of water balanced between enhancing phase separation and avoiding an excessive loss of phenol into the aqueous stream.

In general, the amount of water by volume is in excess over the amount of hydrocarbon by weight. A volume ratio of water to hydrocarbon in the phase separable crude phenol bottoms stream ranging from 1.1:1 to 3:1 is suitable, with a ratio of about 1.5:1 to 2.5:1 being more preferred, and a ratio of about 2:1 being most preferred.

Water can be added as a liquid or vapor, preferably as a liquid. Water can also be added as a fresh stream or as a recycle stream originating from the bottoms phase separator (80), preferably the latter. Water may be added before, simultaneous to, or after the diluent is added. In one embodiment, water is added to the diluted crude phenol bottoms stream through line (82) originating from a bottoms phase separator (80). A typical non-limiting example of the water stream composition comprises 90–95 wt. % water, 3–7 wt. % salts of neutralization, and 0.5–3 wt. % of phenol.

In another advantageous embodiment of the invention, there is provided a process for making a phase separable hydrocarbon stream comprising separating an aralkyl hydroperoxide cleavage mass containing salts of neutralization into a ketone stream and a phenol stream containing the salts, optionally concentrating the phenol stream by further distillation, and forming a phase separable hydrocarbon stream by adding water at a net amount of 5 parts by weight per hour or less to the phenol stream, optionally concentrated. While more water can be added, as mentioned above, the net addition of water should be kept low to avoid treating larger amounts of water downstream. More preferably, only 2 net parts by weight per hour or less, most preferably 1 part by weight per hour or less, and even 0.5 net parts by weight per hour, or less, of water needs to be added to make a phase separable hydrocarbon stream, each based on a flow of 100 parts by weight per hour of all ingredients in the aralkyl hydroperoxide cleavage mass to the splitter (30). The minimum net amount of water added to the phenol stream, optionally concentrated, is an amount sufficient to phase separate a phase separable hydrocarbon stream into a hydrocarbon phase and an aqueous phase containing at least about 80 wt. % of the salts of neutralization in less than one hour residence time.

Once water and the diluent are added to the crude phenolic bottoms stream to form a phase separable crude phenolic bottoms stream, the ingredients are optionally but preferably thoroughly mixed. Any means of mixing is suitable, including static mixing, turbulent in-line mixing, or agitation through a variable speed mixer, depicted in FIG. 1 as the CPC bottoms mixer (70). As shown in FIG. 1, the phase separable crude phenolic bottoms stream enters the CPC bottoms mixer (70) through line (64) to provide sufficient mixing to contact the diluent with as much water as possible, thereby transferring phenol solubilized in the water phase into the hydrocarbon phase. If desired, the stream may be micro-emulsified. The well mixed stream then enters the bottoms phase separator (80) through line (71).

In one embodiment of the invention, the composition of the phase separable crude phenolic bottoms stream entering the separator (80) comprises at least 40 wt. % water, less than 20 wt. % phenolic compounds, alkali metal salts in an amount of at least 1.5 wt. %, phenolic tars, and α-methyl styrene dimers, wherein the volume ratio of water to all ingredients in the composition other than water is 3:1 or less. In a more preferred embodiment, the composition of the phase separable crude phenolic bottoms stream comprises 50 wt. % or more of water, greater than 5 wt. % cumene, greater than 0.5 wt. % AMS, less than 10 wt. % phenol, phenolic tars present in an amount of less than 8 wt. %, and AMSd present in an amount of less than 5 wt. %. In a most preferred embodiment, the weight range of ingredients in the phase separable crude phenolic bottoms composition is as follows:

| | |
|---|---|
| AMS: | 0.5–8 wt. % |
| Cumene: | 5–15 wt. % |
| Phenol: | 3–10 wt. % |
| AP: | 3–10 wt. % |
| DMBA: | 0.2–4 wt. % |

-continued

| | |
|---|---|
| CP: | 3–10 wt. % |
| AMSd: | 1–5 wt. % |
| Tars/Heav: | 3–8 wt. % |
| Salts: | 2–5 wt. % |
| Water: | 50–75 wt. % |

Any means of phase separating the hydrocarbon phase from the aqueous phase in the phase separable crude phenolic bottoms stream is suitable. As depicted in FIG. 1, there is provided a bottoms phase separator vessel (80) wherein the phase separable crude phenolic bottoms stream is injected as a spray into one end of the vessel and allowed to phase separate by settling and flotation over time without agitation into the hydrocarbon phase and aqueous phase.

While the temperature and pressure within the bottoms phase separator (80) may be advantageously lowered compared to the up-stream temperature and pressure conditions in order to promote phase separation, the temperature desirably remains above 100° C. to keep the viscosity of the liquid composition low and preferably to provide an optimal density gradient between the hydrocarbon phase and the aqueous phase. Thus, temperatures exceeding the boiling point of water are preferred, especially temperatures above 110° C., most preferably from 115° to 140° C. The pressure inside the vessel should be kept sufficiently high to retain the composition in a liquid phase when the temperatures exceed the boiling point of any ingredient at atmospheric pressure. Preferably, the pressure is set from 2 psig to 100 psig, most preferably from 35 psig to 70 psig. The residence time within the separator depends upon the composition of the stream and the conditions inside the separator. In general, a residence time of 5 to 60 minutes is sufficient to effectuate phase separation.

Since the process of the invention does not require a phase separator to process large quantities of feed to separate and discharge 80 wt. % or more of the salts of neutralization from the phase separator as a salty aqueous purge stream, the vessel can be advantageously sized. In particular, at least 80 wt. % of the salts of neutralization can be removed from the process in a vessel sized at only 5000 gallons or less, even 3500 gallons or less, based on a cleavage mass feed of 100 parts by weight per hour to the splitter (30).

Once the aqueous phase is separated from the hydrocarbon phase, it is withdrawn as a bottoms stream through line (82), and the less dense upper layer hydrocarbon stream is withdrawn from the bottoms phase separator through line (81) to the heavy ends cracker (90). Through phase separation, the amount of salts of neutralization present in the hydrocarbon phase is reduced compared to the amount of salts of neutralization present prior to phase separation, or the amount of salts present in the neutralized aralkyl hydroperoxide cleavage mass stream or the crude phenolic stream. In one embodiment, at least 80%, more preferably at least 90 wt. %, of the salts present in the crude phenolic bottoms stream are removed from the hydrocarbon phase and transferred to the aqueous phase. As much a 94 wt. % or more of the salts of neutralization are removed from the process of the invention as a salty aqueous purge stream.

At least a portion of the aqueous stream separated from the hydrocarbon phase is purged from the process as a waste stream for treatment if necessary. Preferably, a portion of the aqueous phase is recirculated through line (82) to line (62) or (63) and used as the water source, along with a fresh feed of water in line (84) to make up for water lost through the salt water purge, for addition to the crude phenolic bottoms stream, and another portion of the aqueous phase is purged as a salt water purge through line (83).

An advantage of the process of the invention is that the amount of water containing salts of neutralization discharged at any step downstream from the stripping column is low while simultaneously removing substantial amounts of salts of neutralization from the process. In particular, the process of the invention enables one to discharge and purge a net amount of an aqueous phase containing salts of neutralization at a rate of less than 5 parts by weight per hour based on 100 parts by weight per hour of the aralkyl hydroperoxide cleavage mass stream. Even at this low discharge rate, at least 80 wt. %, preferably 90 wt. % or more, of the salts of neutralization present at any stage from the aralkyl hydroperoxide cleavage mass stream composition immediately prior to entry into the splitter forward are removed. In a more preferred embodiment, the net amount of aqueous phase discharged is less than 1.5 parts by weight per hour, and even less than 1, more preferably less than 0.5, and most preferably less than 0.3 parts by weight per hour each based on 100 parts by weight per hour of the aralkyl hydroperoxide cleavage mass stream composition immediately prior to entry into the splitter. Accordingly, the process consumes only small quantities of waste water, leading to other advantages including a reduction in the amount of water that must be treated and a reduction in the amount of phenol lost to a water purge. The removal of salts of neutralization in the process of the invention is also not dependent on the stability of the composition profile throughout the splitter column.

The process according to the invention also concentrates the amount of salt in the salty aqueous purge stream (83). The process according to the invention can achieve salt concentrations of at least 3 wt. % in at least 90 wt. % water, more preferably at least 4 or even at least 5 wt. % of salts of neutralization based on the weight of the salty aqueous purge stream. A typical composition of the purge aqueous stream in line (83) comprises 90–95 wt. % water, 3–7 wt. % salts of neutralization, and 0.5–3 wt. % of phenol.

The hydrocarbon stream in line (81) is introduced into a heavy ends cracker (90) where the hydrocarbon stream is separated into a light ends stream enriched in phenolic compounds over the phase separated hydrocarbon stream, and a tarry stream enriched in tars over the phase separated hydrocarbon stream, wherein the tarry stream has a reduced amount of salts of neutralization relative to the crude phenolic stream. The cracker may optionally generate light ends which are included in the light ends stream enriched in phenolic compounds.

The hydrocarbon phase exiting as a stream through line (81) has a typical composition comprising:

| | |
|---|---|
| AMS: | 3–10 wt. % |
| Cumene: | 10–40 wt. % |
| Phenol: | 5–25 wt. % |
| AP: | 7–20 wt. % |
| DMBA: | 1–5 wt. % |
| CP: | 7–20 wt. % |
| AMSd: | 3–10 wt. % |
| Tars/Heav: | 6–20 wt. % |
| Salts: | 0.005–0.02 wt. % |

Heavy ends such as un-cracked AP, CP, AMSd, and tars/heavies, and a very small amount of phenol are removed from the bottoms of the heavy ends cracker (90). Since the amount of salts are low, fouling of bottoms of the heavy ends cracker is substantially reduced. Further, fouling of the reboilers which re-circulate a portion of the heavy ends cracker bottoms stream back to the heavy ends cracker, as well as fouling of other equipment for treating the heavy bottoms tar stream exiting through line (92), is substantially reduced. Accordingly, the heavy ends bottom stream exiting the heavy ends cracker is usable as fuel for boilers. Lighter ends in the hydrocarbon stream such as AMS, cumene, phenol, water, and the cracked products of DMBA, CP, AMSd, and tars/heavy oligomers, exit the heavy ends cracker as an overhead through line (91).

In another embodiment of the invention, at least a portion of the light ends stream is recirculated back to the neutralization zone where the aralkyl hydroperoxide cleavage mass is neutralized. This is preferably accomplished by first purifying the lighter ends stream. The lighter ends composition is fed through line (91) to a rectifier (100). Very light ingredients such as benzene, propane, and water are removed from the overhead of the rectifier through line (101), while higher boiling compounds such as phenol, cumene, and AMS, and minor amounts of ethyl benzene exit the bottoms of the rectifier through line (102), at least a portion or all of which is recycled back to the neutralizer (10) through line (1). This will further enhance the ability of the composition in line 1 to phase separate in vessel (20) once neutralized, partially or wholly, in neutralizer (10).

What is claimed is:

1. A process for the manufacture of phenolic compounds comprising:
   a) separating a neutralized aralkyl hydroperoxide cleavage mass stream containing salts of neutralization into a crude ketone stream and a crude phenolic stream containing the salts of neutralization;
   b) separating the crude phenolic stream into a concentrated phenolic-rich stream, enriched in phenolic compounds, and a crude phenolic bottoms stream enriched in tars and alpha methyl styrene dimers, each compared to the crude phenolic stream, said crude phenolic bottoms stream containing salts of neutralization;
   c) to the crude phenolic bottoms stream, adding water and a diluent composition, thereby forming a phase separable crude phenolic bottoms stream, said diluent composition comprised of hydrocarbons phase compatible with the crude phenolic bottoms stream and having a combined density lower than the density of the crude phenolic bottoms stream;
   d) separating the separable crude phenolic bottoms stream into a hydrocarbon phase and an aqueous phase containing salts of neutralization;
   whereby the amount of salts of neutralization in the hydrocarbon phase is reduced compared to the amount of salts of neutralization present prior to separation.

2. The process of claim 1, wherein the weight ratio of diluent composition to crude phenolic bottoms stream is at least 0.15:1.

3. The process of claim 2, wherein the weight ratio of diluent composition to crude phenolic bottoms stream is at least 0.3:1.

4. The process of claim 1, wherein the volume ratio of water to crude phenolic bottoms stream is at least 1:1.

5. The process of claim 1 wherein (c) comprises:
   (i) adding the diluent composition to the crude phenolic bottoms stream thereby forming a diluted crude phenolic bottoms stream, and (ii) subsequently mixing water with the diluted crude phenolic bottoms stream, thereby forming a separable crude phenolic bottoms stream.

6. The process of claim 5, wherein the ratio of diluent to crude phenolic bottoms stream is at least 0.3:1, and the volume ratio of water to diluted crude phenolic bottoms stream ranges from 1.5:1 to 3:1.

7. The process of claim 6, wherein the diluent composition comprises less than 20 wt. % of phenolic compounds.

8. The process of claim 7, wherein the diluent composition comprises cumene and α-methyl styrene.

9. The process of claim 6, further comprising:
(i) separating said crude ketone stream into a concentrated ketone-rich stream, enriched in ketone over the crude ketone stream, and a crude ketone bottoms stream;
(ii) feeding at least a portion of the crude ketone bottoms stream as said diluent composition to the crude phenolic bottoms stream in step c).

10. The process of claim 9, further comprising feeding a portion of said crude ketone bottoms stream to a neutralization zone for neutralization of an aralkyl hydroperoxide cleavage mass.

11. The process of claim 6, wherein a portion of said aqueous phase in step d) is recirculated and used as the water in step (c)(ii), and a portion of the aqueous phase is purged as a salt water purge.

12. The process of claim 11, wherein the salt water purge contains at least 80 wt. % of salts present in the crude phenolic bottoms stream.

13. The process of claim 6, wherein at least 90% of the salts present in phase separable crude phenolic bottoms stream prior to separation are removed from said hydrocarbon phase.

14. The process of claim 1, wherein said separation in step d) is conducted in a phase separation vessel at a temperature above 110° C. and a pressure sufficient to keep the separable crude phenolic bottoms stream in the liquid phase.

15. The process of claim 1, further comprising:
(e) separating said hydrocarbon phase into a light ends stream, enriched in phenolic compounds, and a tarry stream enriched in tars, said tarry steam having a reduced amount of salts of neutralization relative to the crude phenolic stream.

16. The process of claim 15, wherein at least a portion of said light ends stream is re-circulated to a neutralization zone in which an aralkyl hydroperoxide cleavage mass is neutralized.

17. A process for the manufacture of phenolic compounds comprising wholly or partially neutralizing an aralkyl hydroperoxide cleavage mass containing an acid and having a pH of less than 6 in the neutralization zone, thereby forming an aqueous neutralized aralkyl hydroperoxide cleavage mass containing salts of neutralization, subsequently separating said aqueous neutralized aralkyl hydroperoxide cleavage mass into an aqueous stream and a neutralized aralkyl hydroperoxide cleavage mass stream containing a smaller amount of salts than in the aqueous stream, subsequently separating the aralkyl hydroperoxide cleavage mass into a crude ketone stream and a crude phenolic stream containing the salts, separating said crude acetone stream into a concentrated ketone rich stream and a crude ketone bottoms stream, separating said crude phenolic stream into a concentrated phenolic-rich stream and a crude phenolic bottoms stream, separating the crude phenolic bottoms stream into a light ends stream and a tarry stream containing an amount of salts reduced by at least 90% of the amount of salts contained in the crude phenolic bottoms stream, and recycling at least a portion of said crude ketone bottoms stream and at least a portion of said light ends stream as feeds to said aralkyl hydroperoxide cleavage mass, said aqueous neutralized aralkyl hydroperoxide cleavage mass, or to both.

18. The process of claim 17, wherein at least a portion of said crude ketone bottoms stream and at least a portion of said light ends stream are recycled to said aralkyl hydroperoxide cleavage mass prior to neutralization.

19. The process of claim 1, wherein all or a portion of the aqueous stream is purged as an aqueous purge stream from the process, and the total amount of the aqueous purge stream containing salts of neutralization is less than 5 parts by weight per hour based on 100 parts by weight per hour of the aralkyl hydroperoxide cleavage mass stream.

20. The process of claim 19, wherein the net amount of aqueous purge stream discharged from the process is less than 1 part by weight per hour.

21. A process for manufacturing phenolic compounds comprising feeding a wholly or partially neutralized aralkyl hydroperoxide cleavage mass containing salts of neutralization to a splitter, separating acetone and phenol from said cleavage mass in the splitter, leaving a crude phenol bottoms stream, feeding to a phase separation vessel a mixture comprising all or a portion of said crude phenol bottoms stream together with an organic diluent having a first density sufficiently less than a second density of said phenol bottoms stream to phase separate phenol from said mixture into an organic phase comprising said diluent at a weight ratio of organic diluent to crude phenolic bottoms stream of from 0.45:1 to 0.6:1, allowing said mixture to phase separate, and recovering said phenolic compounds in said organic phase, wherein at least 80 wt. % of said salts of neutralization are removed in one or more aqueous streams and wherein said first density is at least about 2 pcf less than said second density.

22. A process for manufacturing phenolic compounds comprising feeding a wholly or partially neutralized aralkyl hydroperoxide cleavage mass containing salts of neutralization to a splitter, separating acetone and phenol from said cleavage mass in the splitter, leaving a crude phenol bottoms stream, feeding to a phase separation vessel a mixture comprising all or a portion of said crude phenol bottoms stream together with an organic diluent having a first density sufficiently less than a second density of said phenol bottoms stream to phase separate phenol from said mixture into an organic phase comprising said diluent at a weight ratio of organic diluent to crude phenolic bottoms stream of from 0.45:1, allowing said mixture to phase separate, and recovering said phenolic compounds in said organic phase, wherein at least 80 wt. % of said salts of neutralization are removed in one or more aqueous streams and wherein said first density is at least about 2 pcf less than said second density.

23. A process for manufacturing phenolic compounds comprising feeding a wholly or partially neutralized aralkyl hydroperoxide cleavage mass containing salts of neutralization to a splitter, separating acetone and phenol from said cleavage mass in the splitter, leaving a crude phenol bottoms stream, feeding to a phase separation vessel a mixture comprising all or a portion of said crude phenol bottoms stream together with an organic diluent having a first density sufficiently less than a second density of said phenol bottoms stream to phase separate phenol from said mixture into an organic phase comprising said diluent at a weight ratio of organic diluent to crude phenolic bottoms stream of at least 0.3:1, allowing said mixture to phase separate, and recovering said phenolic compounds in said organic phase, wherein at least 80 wt. % of said salts of neutralization are removed in one or more aqueous streams and wherein said first density is at least about 2 pcf less than said second density.

24. A process for manufacturing phenolic compounds comprising feeding a wholly or partially neutralized aralkyl hydroperoxide cleavage mass containing salts of neutralization to a splitter, separating acetone and phenol from said cleavage mass in the splitter, leaving a crude phenol bottoms stream, feeding to a phase separation vessel a mixture comprising all or a portion of said crude phenol bottoms stream together with an organic diluent having a first density sufficiently less than a second density of said phenol bottoms stream to phase separate phenol from said mixture into an organic phase comprising said diluent at a weight ratio of organic diluent to crude phenolic bottoms stream of at least 0.15:1, allowing said mixture to phase separate, and recovering said phenolic compounds in said organic phase, wherein at least 80 wt. % of said salts of neutralization are removed in one or more aqueous streams and wherein said first density is at least about 2 pcf less than said second density.

25. A process for manufacturing phenolic compounds comprising:
means for separating a neutralized aralkyl hydroperoxide cleavage mass stream comprising salts of neutralization to produce a crude phenolic stream comprising said salts of neutralization;
means for separating said crude phenolic stream to produce a concentrated phenolic-rich stream and a crude phenolic bottoms stream comprising said salts of neutralization and a remainder of said phenolic compounds;
means for phase separating at least a portion of said remainder of said phenolic compounds from said crude phenolic bottoms stream into an organic phase comprising an organic diluent, said means comprising treating said a crude phenolic bottoms stream with a first quantity of water and with a second quantity of said organic diluent.

26. The method of claim 25 wherein said organic phase comprises an organic diluent at a weight ratio of organic diluent to said crude phenolic bottoms stream of from 0.45 to 0.6:1.

27. The method of claim 25 wherein said organic phase comprises an organic diluent at a weight ratio of organic diluent to said crude phenolic bottoms stream of at least 0.3:1.

28. The method of claim 25 wherein said organic phase comprises an organic diluent at a weight ratio of organic diluent to crude phenolic bottoms stream of at least 0.15:1.

29. The method of claim 25 wherein said means for producing a crude phenol bottoms stream comprises producing a partially or wholly neutralized aralkyl hydroperoxide cleavage mass, and at least 80 wt. % of the salts of neutralization present in said partially or wholly neutralized aralkyl hydroperoxide cleavage mass are removed through one or more aqueous streams.

30. The method of claim 25 wherein said means for producing a crude phenol bottoms stream comprises producing a partially or wholly neutralized aralkyl hydroperoxide cleavage mass, and removing at least 90 wt. % of the salts of neutralization present in said partially or wholly neutralized aralkyl hydroperoxide cleavage mass through one or more aqueous streams.

31. The method of claim 26 wherein said means for producing a crude phenol bottoms stream comprises producing a partially or wholly neutralized aralkyl hydroperoxide cleavage mass, and removing at least 80 wt. % of the salts of neutralization present in said partially or wholly neutralized aralkyl hydroperoxide cleavage mass through one or more aqueous streams.

32. The method of claim 26 wherein said means for producing a crude phenol bottoms stream comprises producing a partially or wholly neutralized aralkyl hydroperoxide cleavage mass, and removing at least 90 wt. % of the salts of neutralization present in said partially or wholly neutralized aralkyl hydroperoxide cleavage mass through one or more aqueous streams.

33. The method of claim 27 wherein said means for producing a crude phenol bottoms stream comprises producing a partially or wholly neutralized aralkyl hydroperoxide cleavage mass, and removing at least 80 wt. % of the salts of neutralization present in said partially or wholly neutralized aralkyl hydroperoxide cleavage mass through one or more aqueous streams.

34. The method of claim 27 wherein said means for producing a crude phenol bottoms stream comprises producing a partially or wholly neutralized aralkyl hydroperoxide cleavage mass, and removing at least 90 wt. % of the salts of neutralization present in said partially or wholly neutralized aralkyl hydroperoxide cleavage mass through one or more aqueous streams.

35. The method of claim 28 wherein said means for producing a crude phenol bottoms stream comprises producing a partially or wholly neutralized aralkyl hydroperoxide cleavage mass, and removing at least 80 wt. % of the salts of neutralization present in said partially or wholly neutralized aralkyl hydroperoxide cleavage mass through one or more aqueous streams.

36. The method of claim 28 wherein said means for producing a crude phenol bottoms stream comprises producing a partially or wholly neutralized aralkyl hydroperoxide cleavage mass, and removing at least 90 wt. % of the salts of neutralization present in said partially or wholly neutralized aralkyl hydroperoxide cleavage mass through one or more aqueous streams.

37. A process for manufacturing phenolic compounds comprising:
separating acetone and phenol from a wholly or partially neutralized aralkyl hydroperoxide cleavage mass comprising salts of neutralization to produce a crude phenolic stream comprising said salts of neutralization;
separating said crude phenolic stream to produce a concentrated phenolic-rich stream and a crude phenol bottoms stream, said crude phenol bottoms stream comprising said salts of neutralization and a remainder of said phenolic compounds;
treating said crude phenol bottoms stream with a first quantity of water and with a second quantity of an organic diluent, said second quantity being effective to solubilize said remainder of said phenolic compounds, producing a mixture;
allowing said mixture to phase separate, recovering said phenolic compounds in an organic phase comprising said organic diluent.

38. The method of claim 37 wherein said organic diluent has a first density sufficiently less than a second density of phenol to phase separate said remainder of said phenolic compounds from said mixture into an organic phase comprising said organic diluent.

39. The method of claim 37 wherein said first density is at least about 1 pcf less than said second density.

40. The method of claim 37 wherein said first density is at least about 2 pcf less than said second density.

41. The method of claim 37 wherein said organic diluent comprises a combined hydrocarbon density of from about 51 to about 53.5 pcf.

42. The method of claim 37 wherein said organic diluent comprises from about 60 to about 90 wt. % cumene, from about 10 to about 30 wt. % AMS, and less than 10 wt. % other hydrocarbons.

43. The method of claim 41 wherein said organic diluent comprises from about 60 to about 90 wt. % cumene, from about 10 to about 30 wt. % AMS, and less than 10 wt. % other hydrocarbons.

44. The method of claim 37 further comprising removing at least 80 wt. % of the salts of neutralization in one or more aqueous streams.

45. The method of claim 38 further comprising removing at least 80 wt. % of the salts of neutralization in one or more aqueous streams.

46. The method of claim 39 further comprising removing at least 80 wt. % of the salts of neutralization in one or more aqueous streams.

47. The method of claim 40 further comprising removing at least 80 wt. % of the salts of neutralization in one or more aqueous streams.

48. The method of claim 41 further comprising removing at least 80 wt. % of the salts of neutralization in one or more aqueous streams.

49. The method of claim 42 further comprising removing at least 80 wt. % of the salts of neutralization in one or more aqueous streams.

50. The method of claim 43 further comprising removing at least 80 wt. % of the salts of neutralization in one or more aqueous streams.

51. The method of claim 37 further comprising removing at least 90 wt. % of the salts of neutralization in one or more aqueous streams.

52. The method of claim 38 further comprising removing at least 90 wt. % of the salts of neutralization in one or more aqueous streams.

53. The method of claim 39 further comprising removing at least 90 wt. % of the salts of neutralization in one or more aqueous streams.

54. The method of claim 40 further comprising removing at least 90 wt. % of the salts of neutralization in one or more aqueous streams.

55. The method of claim 41 further comprising removing at least 90 wt. % of the salts of neutralization in one or more aqueous streams.

56. The method of claim 42 further comprising removing at least 90 wt. % of the salts of neutralization in one or more aqueous streams.

57. The method of claim 43 further comprising removing at least 90 wt. % of the salts of neutralization in one or more aqueous streams.

58. The method of claim 37 wherein said organic phase comprises an organic diluent at a weight ratio of organic diluent to crude phenolic bottoms stream of from about 0.45:1 to about 0.6:1.

59. The method of claim 37 wherein said organic phase comprises an organic diluent at a weight ratio of organic diluent to crude phenolic bottoms stream of at least 0.3:1.

60. The method of claim 38 wherein said organic phase comprises an organic diluent at a weight ratio of organic diluent to crude phenolic bottoms stream of from about 0.45:1 to about 0.6:1.

61. The method of claim 38 wherein said organic phase comprises an organic diluent at a weight ratio of organic diluent to crude phenolic bottoms stream of at least 0.3:1.

62. The method of claim 39 wherein said organic phase comprises an organic diluent at a weight ratio of organic diluent to crude phenolic bottoms stream of from about 0.45:1 to about 0.6:1.

63. The method of claim 39 wherein said organic phase comprises an organic diluent at a weight ratio of organic diluent to crude phenolic bottoms stream of at least 0.3:1.

64. The method of claim 40 wherein said organic phase comprises an organic diluent at a weight ratio of organic diluent to crude phenolic bottoms stream of from about 0.45:1 to about 0.6:1.

65. The method of claim 40 wherein said organic phase comprises an organic diluent at a weight ratio of organic diluent to crude phenolic bottoms stream of at least 0.3:1.

66. The method of claim 41 wherein said organic phase comprises an organic diluent at a weight ratio of organic diluent to crude phenolic bottoms stream of from about 0.45:1 to about 0.6:1.

67. The method of claim 41 wherein said organic phase comprises an organic diluent at a weight ratio of organic diluent to crude phenolic bottoms stream of at least 0.3:1.

68. The method of claim 42 wherein said organic phase comprises an organic diluent at a weight ratio of organic diluent to crude phenolic bottoms stream of from about 0.45:1 to about 0.6:1.

69. The method of claim 42 wherein said organic phase comprises an organic diluent at a weight ratio of organic diluent to crude phenolic bottoms stream of at least 0.3:1.

70. The method of claim 43 wherein said organic phase comprises an organic diluent at a weight ratio of organic diluent to crude phenolic bottoms stream of from about 0.45:1 to about 0.6:1.

71. The method of claim 43 wherein said organic phase comprises an organic diluent at a weight ratio of organic diluent to crude phenolic bottoms stream of at least 0.3:1.

72. The method of claim 57 wherein said organic phase comprises an organic diluent at a weight ratio of organic diluent to crude phenolic bottoms stream of from about 0.45:1 to about 0.6:1.

73. The method of claim 57 wherein said organic phase comprises an organic diluent at a weight ratio of organic diluent to crude phenolic bottom am of at least 0.3:1.

74. A process for manufacturing phenolic compounds comprising:
  separating acetone and phenol from a wholly or partially neutralized aralkyl hydroperoxide cleavage mass comprising salts of neutralization to produce a crude phenolic stream comprising said salts of neutralization;
  separating said crude phenolic stream to produce a concentrated phenolic-rich stream and a crude phenol bottoms stream, said crude phenol bottoms stream comprising said salts of neutralization and a remainder of said phenolic compounds;
  treating said crude phenol bottoms stream with a first quantity of water and with a second quantity of an organic diluent, said second quantity being effective to solubilize said remainder of said phenolic compounds to produce a mixture, wherein a weight ratio of said organic diluent to said crude phenolic bottoms stream is at least 0.15:1;
  allowing said mixture to phase separate, recovering said phenolic compounds in an organic phase comprising said organic diluent.

75. The method of claim 74 wherein said organic diluent has a first density sufficiently less than a second density of phenol to phase separate said remainder of said phenolic compounds from said mixture into an organic phase comprising said organic diluent.

76. The method of claim 74 wherein said first density is at least about 1 pcf less than said second density.

77. The method of claim 74 wherein said first density is at least about 2 pcf less than said second density.

78. The method of claim 74 wherein said organic diluent comprises a combined hydrocarbon density of from about 51 to about 53.5 pcf.

79. The method of claim 74 wherein said organic diluent comprises from about 60 to about 90 wt. % cumene, from about 10 to about 30 wt. % AMS, and less than 10 wt. % other hydrocarbons.

80. The method of claim 78 wherein said organic diluent comprises from about 60 to about 90 wt. % cumene, from about 10 to about 30 wt. % AMS, and less than 10 wt. % other hydrocarbons.

81. The method of claim 74 further comprising removing at least 80 wt. % of the salts of neutralization in one or more aqueous streams.

82. The method of claim 75 further comprising removing at least 80 wt. % of the salts of neutralization in one or more aqueous streams.

83. The method of claim 76 further comprising removing at least 80 wt. % of the salts of neutralization in one or more aqueous streams.

84. The method of claim 77 further comprising removing at least 80 wt. % of the salts of neutralization in one or more aqueous streams.

85. The method of claim 78 further comprising removing at least 80 wt. % of the salts of neutralization in one or more aqueous streams.

86. The method of claim 79 further comprising removing at least 80 wt. % of the salts of neutralization in one or more aqueous streams.

87. The method of claim 80 further comprising removing at least 80 wt. % of the salts of neutralization in one or more aqueous streams.

88. The method of claim 74 further comprising removing at least 90 wt. % of the salts of neutralization in one or more aqueous streams.

89. The method of claim 75 further comprising removing at least 90 wt. % of the salts of neutralization in one or more aqueous streams.

90. The method of claim 76 further comprising removing at least 90 wt. % of the salts of neutralization in one or more aqueous streams.

91. The method of claim 77 further comprising removing at least 90 wt. % of the salts of neutralization in one or more aqueous streams.

92. The method of claim 78 further comprising removing at least 90 wt. % of the salts of neutralization in one or more aqueous streams.

93. The method of claim 79 further comprising removing at least 90 wt. % of the salts of neutralization in one or more aqueous streams.

94. The method of claim 80 further comprising removing at least 90 wt. % of the salts of neutralization in one or more aqueous streams.

95. A process for manufacturing phenolic compounds comprising:
separating acetone and phenol from a wholly or partially neutralized aralkyl hydroperoxide cleavage mass comprising salts of neutralization to produce a crude phenolic stream comprising said salts of neutralization;
separating said crude phenolic stream to produce a concentrated phenolic-rich stream and a crude phenol bottoms stream, said crude phenol bottoms stream comprising said salts of neutralization and a remainder of said phenolic compounds;
treating said crude phenol bottoms stream with a first quantity of water and a second quantity of an organic diluent, said second quantity being effective to solubilize said remainder of said phenolic compounds producing a mixture, wherein said organic diluent has a first density sufficiently less than a second density of phenol to phase separate said remainder of said phenolic compounds from said mixture into an organic phase comprising said organic diluent;
allowing said mixture to phase separate to produce an organic phase comprising said phenolic compounds and said organic diluent.

96. The method of claim 95 further comprising recovering said phenolic compounds from said organic phase.

97. The method of claim 96 wherein said first density is at least about 1 pcf less than said second density.

98. The method of claim 96 wherein said first density is at least about 2 pcf less than said second density.

99. The method of claim 97 wherein said organic diluent comprises a combined hydrocarbon density of from about 51 to about 53.5 pcf.

100. The method of claim 97 wherein said organic diluent comprises from about 60 to about 90 wt. % cumene, from about 10 to about 30 wt. % AMS, and less than 10 wt. % other hydrocarbons.

101. The method of claim 99 wherein said organic diluent comprises from about 60 to about 90 wt. % cumene, from about 10 to about 30 wt. % AMS, and less than 10 wt. % other hydrocarbons.

102. The method of claim 96 wherein at least 80 wt. % of said salts of neutralization are removed in one or more aqueous streams.

103. The method of claim 97 wherein at least 80 wt. % of said salts of neutralization are removed in one or more aqueous streams.

104. The method of claim 98 wherein at least 80 wt. % of said salts of neutralization are removed in one or more aqueous streams.

105. The method of claim 99 wherein at least 80 wt. % of said salts of neutralization are removed in one or more aqueous streams.

106. The method of claim 100 wherein at least 80 wt. % of said salts of neutralization are removed in one or more aqueous streams.

107. The method of claim 101 wherein at least 80 wt. % of said salts of neutralization are removed in one or more aqueous streams.

108. The method of claim 96 wherein at least 90 wt. % of said salts of neutralization are removed in one or more aqueous streams.

109. The method of claim 97 wherein at least 90 wt. % of said salts of neutralization are removed in one or more aqueous streams.

110. The method of claim 98 wherein at least 90 wt. % of said salts of neutralization are removed in one or more aqueous streams.

111. The method of claim 99 wherein at least 90 wt. % of said salts of neutralization are removed in one or more aqueous streams.

112. The method of claim 100 wherein at least 90 wt. % of said salts of neutralization are removed in one or more aqueous streams.

113. The method of claim 101 wherein at least 90 wt. % of said salts of neutralization are removed in one or more aqueous streams.

114. The method of claim 96 wherein said organic phase comprises an organic diluent at a weight ratio of organic diluent to crude phenolic bottoms stream of from 0.45 to 0.6:1.

115. The method of claim 96 wherein said organic phase comprises an organic diluent at a weight ratio of organic diluent to crude phenolic bottoms stream of at least 0.3:1.

116. The method of claim 96 wherein said organic phase comprises an organic diluent at a weight ratio of organic diluent to crude phenolic bottoms stream of at least 0.15:1.

117. The method of claim 97 wherein said organic phase comprises an organic diluent at a weight ratio of organic diluent to crude phenolic bottoms stream of from 0.45 to 0.6:1.

118. The method of claim 97 wherein said organic phase comprises an organic diluent at a weight ratio of organic diluent to crude phenolic bottoms stream of at least 0.15:1.

119. The method of claim 98 wherein said organic phase comprises an organic diluent at a weight ratio of organic diluent to crude phenolic bottoms stream of from 0.45:1 to 0.6:1.

120. The method of claim 98 wherein said organic phase comprises an organic diluent at a weight ratio of organic diluent to crude phenolic bottoms stream of at least 0.15:1.

121. The method of claim 99 wherein said organic phase comprises an organic diluent at a weight ratio of organic diluent to crude phenolic bottoms stream of from 0.45:1 to 0.6:1.

122. The method of claim 99 wherein said organic phase comprises an organic diluent at a weight ratio of organic diluent to crude phenolic bottoms stream of at least 0.15:1.

123. The method of claim 100 wherein said organic phase comprises 1 an organic diluent at a weight ratio of organic diluent to crude phenolic bottoms stream of from 0.45:1 to 0.6:1.

124. The method of claim 100 wherein said organic phase comprises an organic diluent at a weight ratio of organic diluent to crude phenolic bottoms stream of at least 0.15:1.

125. The method of claim 101 wherein said organic phase comprises 1 an organic diluent at a weight ratio of organic diluent to crude phenolic bottoms stream of from 0.45:1 to 0.6:1.

126. The method of claim 101 wherein said organic phase comprises an organic diluent at a weight ratio of organic diluent to crude phenolic bottoms stream of at least 0.15:1.

127. The method of claim 113 wherein said organic phase comprises 1 an organic diluent at a weight ratio of organic diluent to crude phenolic bottoms stream of from 0.45:1 to 0.6:1.

128. The method of claim 113 wherein said organic phase comprises an organic diluent at a weight ratio of organic diluent to crude phenolic bottoms stream of at least 0.15:1.

\* \* \* \* \*